United States Patent [19]

McCall

[11] 4,267,838

[45] May 19, 1981

[54] APPARATUS FOR ELECTRICAL IMPULSE ACUPRESSURE TREATMENT

[76] Inventor: Francis J. McCall, 16250 Ventura Blvd., Encino, Calif. 91436

[21] Appl. No.: 70,747

[22] Filed: Aug. 29, 1979

[51] Int. Cl.³ .................. A61H 39/04; A61N 1/36
[52] U.S. Cl. .................. 128/303 R; 128/789; 128/907
[58] Field of Search .......... 128/303.13, 303 R, 329 A, 128/419 R, 420 R, 421, 422, 735, 783, 791, 792, 793, 789, 802, 907, 24.4, 24.5, 799, 784

[56] References Cited

U.S. PATENT DOCUMENTS

| | | | |
|---|---|---|---|
| 521,800 | 6/1894 | Leech | 128/789 X |
| 3,108,268 | 10/1963 | Uttal | 128/783 X |
| 3,900,020 | 8/1975 | Lock | 128/735 |
| 3,923,064 | 12/1975 | Leupold | 128/329 A |
| 4,037,590 | 7/1977 | Dohring et al. | 128/303.13 X |
| 4,073,296 | 2/1978 | McCall | 128/303 R |
| 4,112,923 | 9/1978 | Tomecek | 128/419 R |
| 4,180,079 | 12/1979 | Wing | 128/422 |

FOREIGN PATENT DOCUMENTS

| | | | |
|---|---|---|---|
| 2638580 | 3/1978 | Fed. Rep. of Germany | 128/303.13 |
| 2361917 | 3/1978 | France | 128/303.13 |

OTHER PUBLICATIONS

McCall "Auricular ACU Mold Therapy . . . ", p. 1–6, Received PTO Jul. 27, 1977.

*Primary Examiner*—Lee S. Cohen
*Attorney, Agent, or Firm*—Jack C. Munro

[57] ABSTRACT

An electrical pulse acupressure treatment device which provides for the use of a housing which is to be located in a preselected position upon the human body. Embedded within the surface of the housing that is located next to the skin of the human body is a protruding nodule. This nodule is metallic and will normally be spherical in shape. The nodule is to press against an acupuncture point of the human body. An electrical conductor passes through the housing and it attached to the nodule. This electrical conductor is connected to a source of electrical energy. This source of electrical energy is to transmit pulses of electrical energy in a preselected wave pattern to the nodule. This source is electrically adjustable to vary the current to the nodule.

3 Claims, 5 Drawing Figures

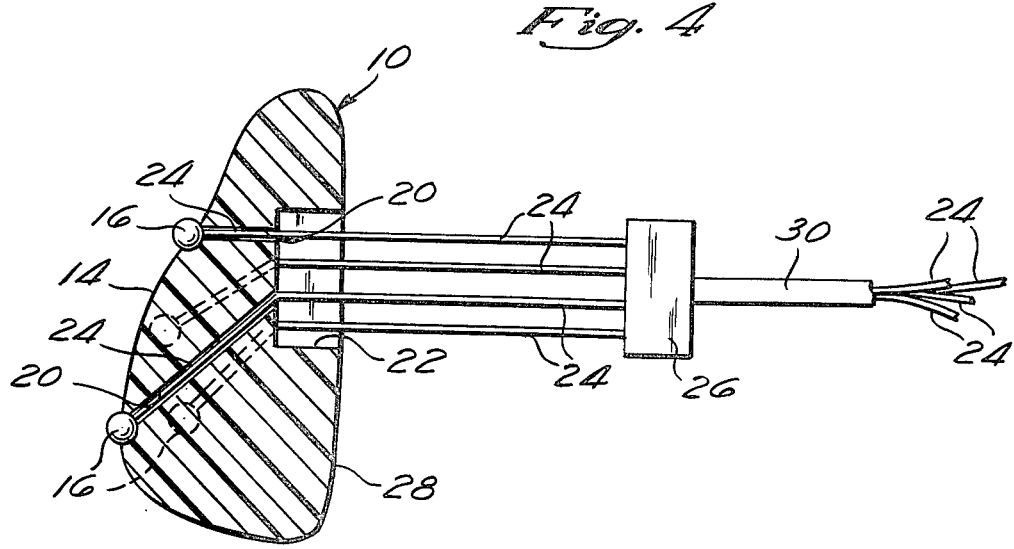
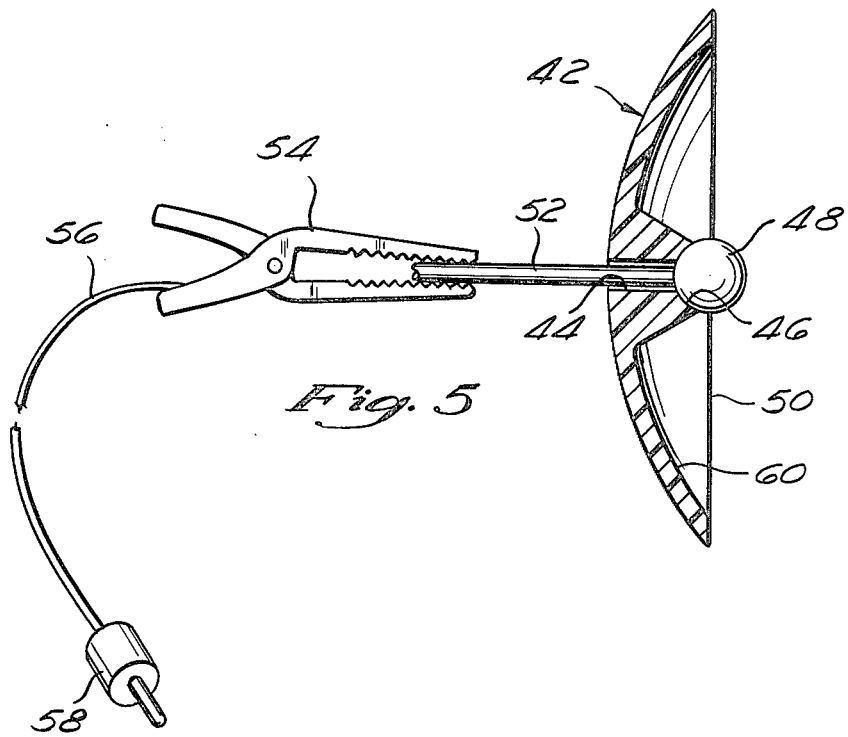

APPARATUS FOR ELECTRICAL IMPULSE ACUPRESSURE TREATMENT

BACKGROUND OF THE INVENTION

The field of this invention relates to acupressure therapy and more particularly to an improved acupressure device in which small electrical impulses are continuously transmitted to selected acupuncture points so that a higher level of treatment can be applied to the patient over an extended period of time.

The subject matter of this invention is to constitute an improvement of the structure defined within U.S. Pat. No. 4,073,296, issued Feb. 14, 1978, entitled APPARATUS FOR ACUPRESSURE TREATMENT, by the same inventor.

As was discussed within the aforementioned patent, it is known that there are certain locations or acupuncture points on the ear and other parts of the body which, when subjected to acupuncture treatment, will have a therapeutic affect on corresponding body functions, reactions, muscles, organs, systems, and the like. For example, one specific acupuncture point on the ear may influence throat reaction, another the mouth function, while still another, stomach activity. Location and stimulation of these sensitive acupuncture points with acupuncture therapy has been used to treat such conditions such as obesity, alcoholism, drug addiction, smoking, and the like.

The common technique for acupuncture therapy is for the practioner to pierce the skin and stimulate the acupuncture point with a fine needle. While this procedure is satisfactory, the stimulation of the acupuncture point occurs only during the time the patient visits the practioner. This obviously minimizes the length of treatment.

It has also been known, as is evidenced by the structure of the aforementioned patent, that it is not necessary to insert needles into the body in order to effect treatment of acupuncture points. Physical pressure applied against the specific point will achieve some degree of treatment and can be as effective as the insertion of a needle. The aforementioned patent disclosed a molded device which was adapted to be located within the external ear. The interior surface of the molded device includes protruding members, which were in the form of spherical nodules. These nodules were specifically placed in conjunction with the molded device so as to be located directly against certain acupuncture points. Therefore, the user, by wearing of this molded device, can incur continuous treatment of these acupuncture points. Therefore, not only can treatment be effected within the practioner's place of business, but also treatment can continue during the time that the patient is not being treated directly by the practioner.

It has been known in the part that not only does physical pressure treat acupuncture points, but also pulses of electrical energy. These pulses are of a very low current level, and actually in most instances, are not even felt by the patient. However, the use of these electrical pulses are believed to provide a more effective method of treatment of the acupuncture point.

SUMMARY OF THE INVENTION

The structure of this invention combines the salient features of both the physical pressure acupressure device and also electrical pulse treating of the acupuncture point. Previous to this invention, there has been no known device which operated in accordance with the present invention. A molded device is specifically attached to a body location, over an acupuncture point. The inside surface of the molded device includes protruding metallic nodules. An electrical conductor is passed through the housing and connects to the nodule. Electrical pulses are transmitted to the nodule in some form of preselected wave pattern. This wave pattern can be varied. The current supplied to the nodule can be varied. Therefore, not only is the acupuncture point being treated by the pressure applied by the nodule against the acupuncture point, but also is being treated by a steady stream of electrical pulses. Therefore, as the patient goes about his daily routine, the particular body function or condition is being continuously treated. Actually, the patient is, in most instances, totally unaware of the treatment.

BRIEF DESCRIPTION OF THE DRAWINGS

FIG. 4 is a cross-sectional view of the molded member taken along line 4—4 of FIG. 2; and FIG. 5 is a diagrammatic view of a different form of molded member which is adapted to be located on a flat skin area of the patient and not within the ear.

DETAILED DESCRIPTION OF THE SHOWN EMBODIMENT

Figure 1:
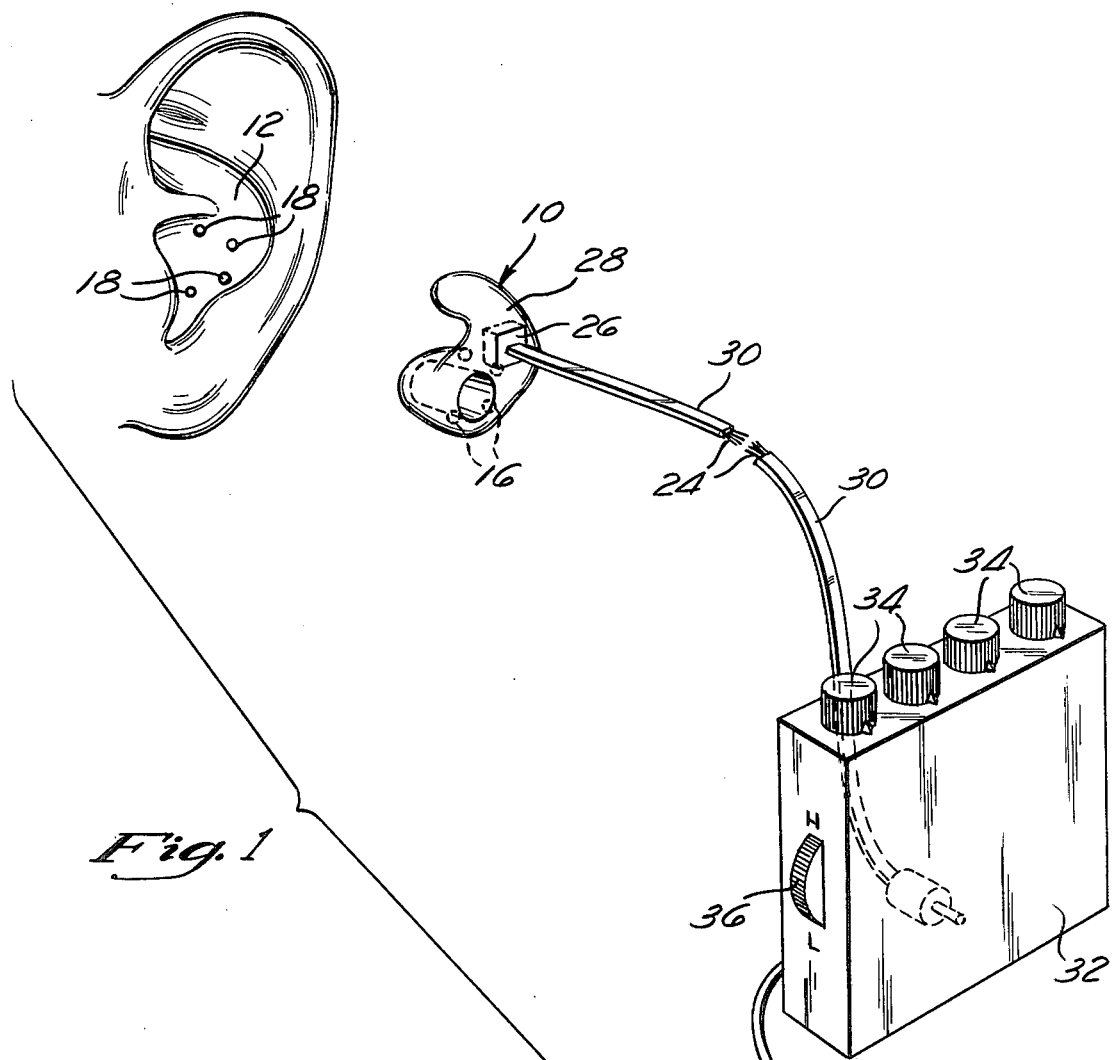
FIG. 1 is a diagrammatic perspective view of the structure of this invention showing the device attached to a molded device which is conformed specifically to be located within the human ear.
Figures 2, 3:
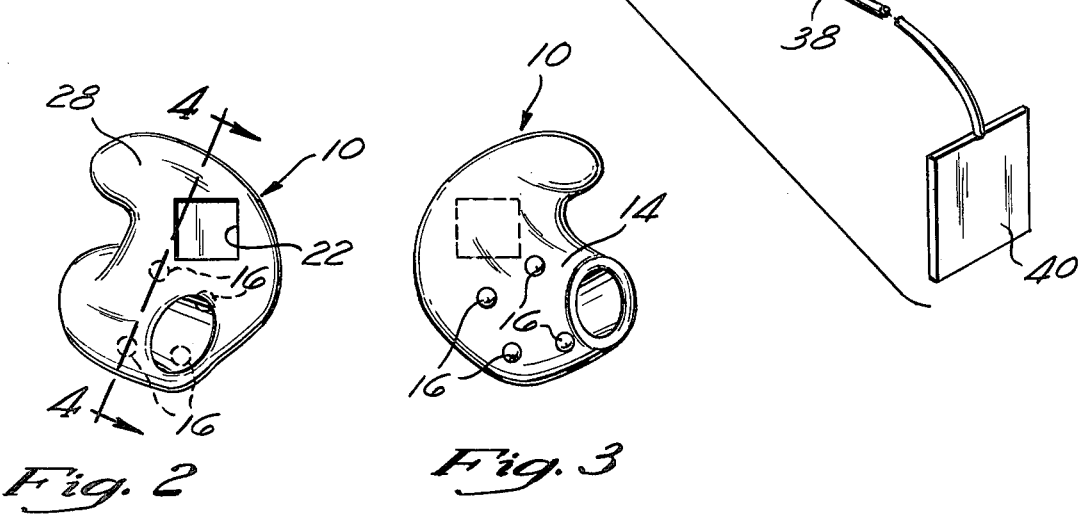
FIG. 2 is a view of the outside surface of the molded member which is to be located within the human ear of FIG. 1.
FIG. 3 is an inside surface view of the molded member of FIG. 1 showing the location of the protruding nodules.

Referring particularly to the drawings, there is shown in FIGS. 1–4 a first embodiment of the device of this invention which employs the use of a housing 10 which is shaped to particularly accommodate the exterior ear 12. The ear mold housing 10 is to be constructed of a plastic, such as methyl methacrylate, ethyl methylacrylate or an acrylic resin. Also, other types of plastic could be employed. The ear mold housing 10 is to be formed individually by the making of an impression from the particular patient. The method of making the ear mold housing 10 is discussed more fully in the aforementioned patent and reference is to be had thereto.

On the inner surface 14 of the mold housing 10, there are positioned a plurality of spaced-apart recesses. Within each recess is located a spherical, metallic nodule 16. It is to be noted that there are four in number of the nodules 16. However, the exact number of the nodules 16 is deemed to be a matter of choice as a lesser or greater number could be employed. It is to be noted that these nodules 16 are to exert pressure onto particular points 18 located within the exterior ear 12. These points 18 are known acupuncture points, with each point being able to functionally control different parts of the patient's body. Each nodule 16 is to be pressed against a particular acupuncture point 18.

Formed within the housing 10 are a plurality of passageways 20. These passageways 20 extend from an enlarged opening 22. A single passageway 20 connects with a single nodule recess within which is located a single nodule 16. An electrical conductor 24 is attached to each nodule 16 with there being a separate electrical conductor 24 for each nodule 16. The electrical conductors 24 are then electrically connected to a junction housing 26. The junction housing 26 is polygonal shaped and fits snugly within the mating polygonal shaped opening 22. The opening 22 is located on the exterior surface 28 of the housing 10.

The four conductors 24 extend exteriorly from the junction box 26 by means of the single electrical conductor 30. The conductors 24 within the same electrical conductor 30 are then electrically connected to a source of electrical energy which takes the form of a box 32. This box 32 is of a size, typically, $2 \times 2 \times 1\frac{1}{2}$ inches to readily fit within a person's pocket located in their clothing. Within the box 32 is to be a conventional battery, not shown. Each conductor 24 is electrically connected to a particular turning knob 34. It is to be noted that there are four in number of the turning knobs 34 with there being a particular knob 34 for each conductor 24. Each turning knob 34 is to operate one particular nodule 16 with another turning knob 34 operating another particular nodule 16, etc. By manually turning of the knobs 34, the amount of electrical current being conducted to the nodule 16 can then be varied. Typically, the current will not exceed 20 milliamperes.

It is to be understood that normally the current being conducted to each nodule 16 is not a continuous direct current. It is intended that the electrical energy be conducted to each nodule 16 in the form of pulses. These pulses can take two forms. The first form is a regular pattern of pulses, wherein the amplitude of each pulse is identical and constant for a set number of microseconds with the current between the pulses diminishing to zero. The second type of pulse is a rise to a certain magnitude and then to steadily diminish over a few microseconds, and then repeat itself. The first type of pulse is for the purpose of sedating the particular area of the body controlled by the particular acupuncture point. The second type of pulse is for what is termed tonification, which is the treating of the particular area of the body, but does not go so far as to sedate it. The selection of the type of pulse is to be achieved manually through the use of control knob 36 mounted within the box 32. If the control knob is moved to position "L", then the second type of pulse will be achieved. If the knob 36 is moved to position "H", the first type of pulse will be achieved.

It is necessary that there is an electrical ground in order for the electrical pulses to have any effect. For this purpose, there is an electrical ground wire 38 which is attached to a one inch by one inch electrical grounding pad 40. This pad 40 is to be taped to a person's body, such as in the chest area, or other similar area.

Referring particularly to FIG. 5 of the drawings, there is shown a modified form of housing 42 which is basically cup-shaped in cross-section. The housing 42 in essence is to be a segment of a sphere. The housing 42 has a central opening 44 which connects with a nodule recess 46. Within the nodule recess 46 is to be located a metallic spherical nodule 48. It is to be noted that the exterior portion of the nodule 48 protrudes beyond the interior plane 50 of the housing 42. The nodule 48 is electrically connected to electrical conductor 52. The electrical conductor 52 connects to an alligator clamp 54. This alligator clamp 54 is electrically connected through electrical conductor 56 to an electrical connecting jack 58. The jack 58 is to extend within an appropriate electrical connection (not shown) within the box 32. Such an electrical connection would, in all probability, be similarly employed to effect interconnection between the electrical conductor 30 and the box 32.

The housing 42 is adapted to be located in areas of the body other than the ear. It can be placed on the arm, leg, hip, or torso, wherever it is desired.

The use of the housing 42 is accomplished in a manner similar to the mold 10. The inner surface of the housing 42 is pressed tightly against the skin which causes the protruding nodule 48 to be physically pressed against the appropriate acupuncture point that it is desired to treat. It is well known that there are acupuncture points other than in the ear and actually, these points are spread throughout the person's body. In order to securely stay in position so that the housing 42 can be left unattended, an adhesive (not shown) is to be placed within the cavity 60 of the housing 42. The use of such adhesives is well known and are commonly used in the medical field. Such an adhesive would securely maintain the position of the housing 42 until it is desired to remove such. It is to be understood that the housing 42 would normally be constructed of a plastic similar to the housing 10.

What is claimed is:

1. An electrical pulse acupressure treatment device comprising:

a plastic molded housing having an interior surface and an exterior surface, said housing adapted to be removably connected to a portion of a human body in a predetermined position relative to acupuncture points of the body;

a plurality of separate metallic nodules imbedded in said interior surface of said plastic molded housing, each of said nodules being positioned on said housing to press against a said acupuncture point and to therefore treat the corresponding body function when said housing is retained in said predetermined position; and an electrical conductor assembly, composed of a plurality of separate electrical conductors, each said nodule being attached to a said electrical conductor with there being a separate elecrical conductor for each said nodule, each said electrical conductor being combined at a junction box, said junction box being polygonal shaped, a polygonal shaped recess formed in said exterior surface of said plastic molded housing, said junction box tightly fitting within said polygonal shaped recess, a source of electrical energy to produce electrical pulses, said electrical conductors being electrically connected to said source of electrical energy, said source of electrical energy being of a size to be readily carried by a human being, said electrical conductors to transmit said electrical pulses to said nodules.

2. The device as defined in claim 1 wherein;
said source of electrical energy includes means to vary the emitted type of electrical energy.

3. The device as defined in claim 2 wherein:
each said nodule being spherical in shape.

* * * * *